United States Patent [19]

Reynolds

[11] Patent Number: 4,766,895

[45] Date of Patent: Aug. 30, 1988

[54] APPARATUS FOR CORNEAL CURVATURE ADJUSTMENT

[75] Inventor: Alvin E. Reynolds, Tulsa, Okla.

[73] Assignee: Kera Corneal Devices, Inc., Santa Clara, Calif.

[21] Appl. No.: 10,400

[22] Filed: Feb. 3, 1987

Related U.S. Application Data

[62] Division of Ser. No. 579,480, Feb. 23, 1984, Pat. No. 4,671,276, which is a division of Ser. No. 336,919, Jan. 4, 1982, Pat. No. 4,452,235.

[51] Int. Cl.⁴ .............................................. A61B 17/00
[52] U.S. Cl. ................................. 128/303 R; 128/330
[58] Field of Search .................. 128/303 R, 330, 340, 128/305

[56] References Cited

U.S. PATENT DOCUMENTS 3,074,407  1/1963  Moon et al. .................... 128/303 R Primary Examiner—Michael H. Thaler
Attorney, Agent, or Firm—Head & Johnson

[57] ABSTRACT

In a system for adjusting the curvature of the cornea of the eye involving the insertion of a plastic split end adjusting ring into the stroma of the cornea, a holder has a concave end surface and circular groove therein for receiving a metal dissecting ring and for holding it in a circular shape. As the holder is rotated the inserted end of the metal ring is magnetically forced to follow rotation of the holder thus the dissecting ring is inserted in a circular path within the stroma.

4 Claims, 4 Drawing Sheets

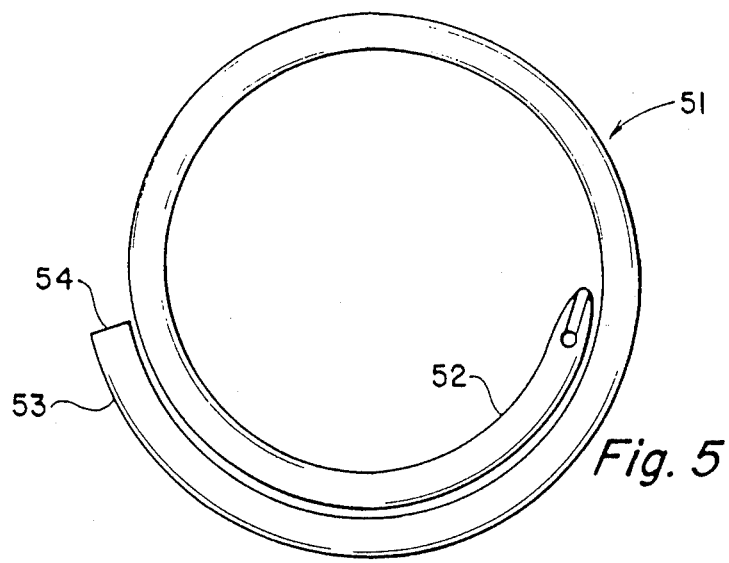
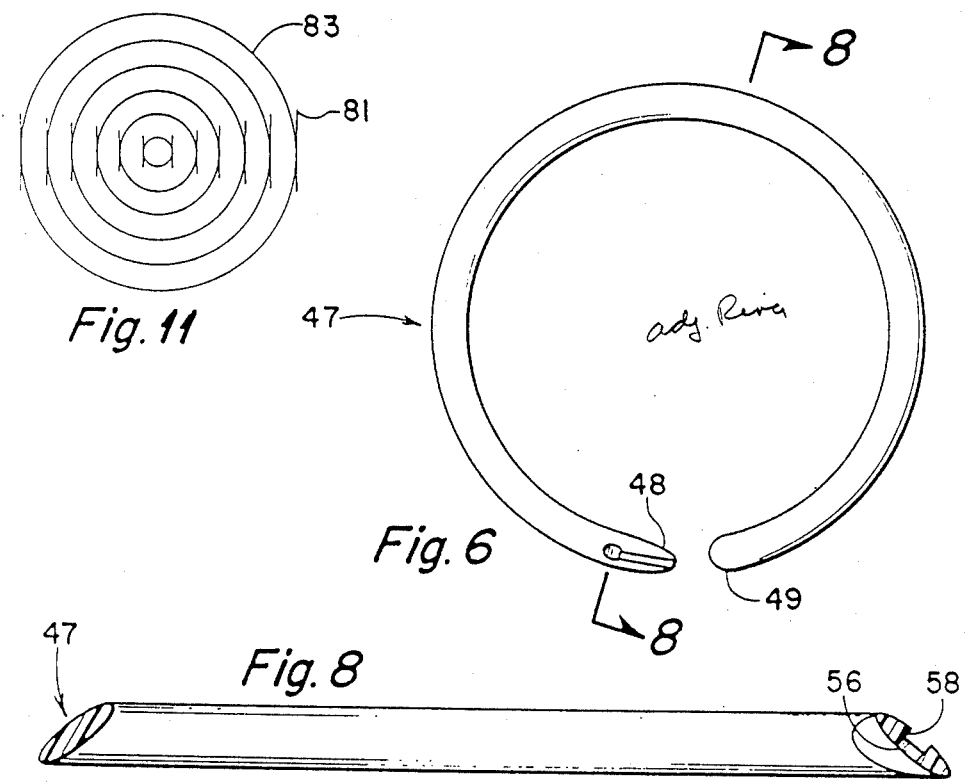

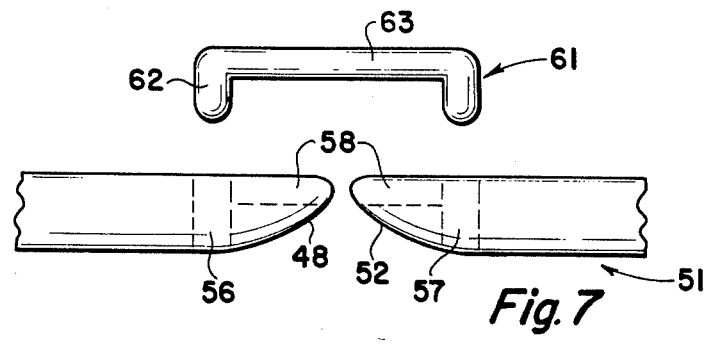
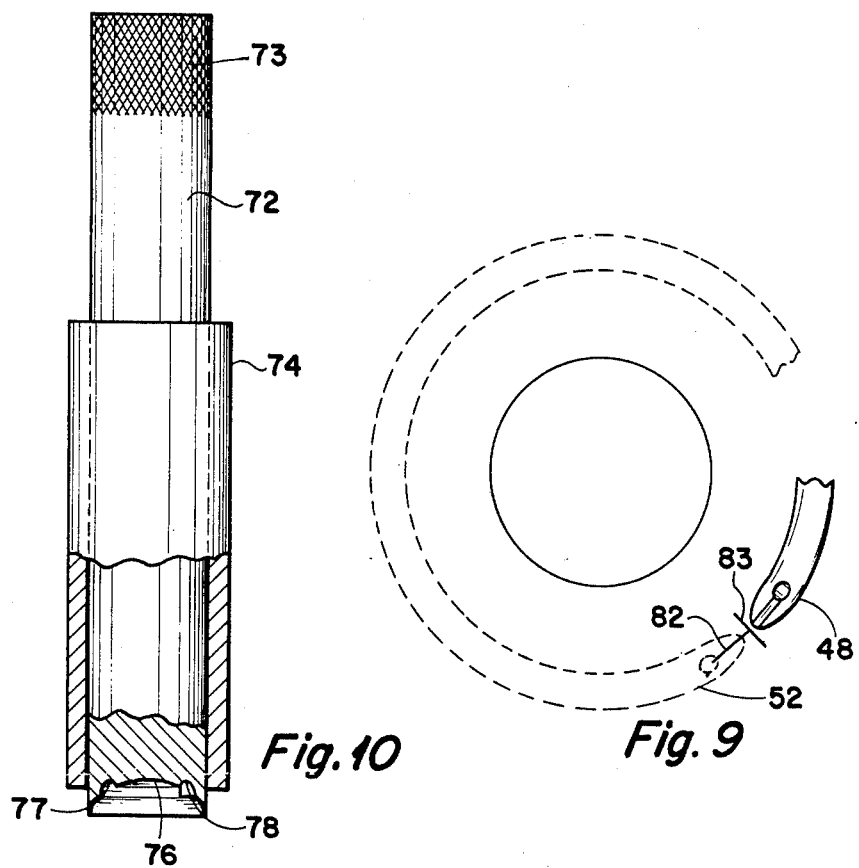

APPARATUS FOR CORNEAL CURVATURE ADJUSTMENT

This is a divisional of co-pending application Ser. No. 579,480, filed on Feb. 23, 1984, now U.S. Pat. No. 4,671,276, which is a divisional of U.S. Pat. No. 4,452,235, filed as Ser. No. 336,919 on Jan. 4, 1982.

BACKGROUND OF THE INVENTION

This invention relates to a method and apparatus for adjusting the shape of components of the eye and more particularly to making fixed changes in the corneal curvature.

Deviations form the normal shape of the corneal surface produce errors of refraction in the visual process. The eye in a state of rest, without accomodation, focuses the image of distant objects exactly on the retina. Such an eye enjoys distinct vision for distant objects without effort. Any variation from this standard constitutes ametropia, a condition in which the eye at rest is unable to focus the image of a distant object on the retina. Hyperopia is an error of refraction in which, with the eye at rest, parallel rays from distant objects are brought to focus behind the retina. Divergent rays from near objects are focused still further back. In one aspect of hypertopia, the corneal surface is flattened which decreases the angle of refraction of rays as they pass through the refractive surfaces of the cornea, causing a convergence or focus of the rays at a point behind the retina. The retina is comprised partially of nerve fibers which are an expansion of the optic nerve. Waves of light falling on the retina are converted into nerve impulses and carried by the optic nerve to the brain to produce the sensation of light. To focus parallel rays on the retina, the hyperopic eye must either accomodate, i.e., increase the convexity of its lens, or a convex lens of sufficient strength to focus rays on the retina must be placed before the eye.

Myopia is that refractive condition in which, with accomodation completely relaxed, parallel rays are brought to focus in front of the retina. One condition which commonly causes myopia is when the corneal curvature is steepened, thus the refraction of rays is greater as they pass through the refractive surfaces of the cornea, and the over refracted rays converge or focus in front of the retina in the vitreous of the eye. When the rays reach the retina they become divergent, forming a circle of diffusion and consequently a blurred image. A concave lens is used to correct the focus of the eye for myopia.

The normal treatment of these classic forms of refractive error of the eye is with the use of eyeglasses or contact lenses, both of which have well-known disadvantages to the user. Recent research has been directed to operative techniques to change the refractive condition of the eye. Such techniques are generally referred to "keratorefractive techniques". Two such techniques are more particularly called keratophakia and keratomileusis. Keralomileusis involves the regrinding of a corneal lamella into a meniscus or hyperopic lens to correct myopia or hyperopia. A corneal optical lathe has been especially developed for this procedure and is also used in the keratophakia procedure, when a homograft ground into a convex lens is placed interlamellarly to correct aphakic hypermetropia. The homograft tissue (corneal lamella) is frozen with carbon dioxide. The homograft is cut as a contact lens would be, i.e., to the optical power required to effect the desired optical correction of the cornea. In keratomileusis, the anterior corneal lamella is shaped by the lathe and in keratophobia, it is the corneal stroma of a donor eye that is shaped by the lathe. These techniques have a broad application in the correction of high hyperopic and myopic errors. These procedures require radial cutting of the cornea about the periphery of the graft which weakens the cornea so that pressure from fluids below the incisions pushes up under the cuts and flattens the curvature of the cornea. This flattening of the cornea results in refractive errors to the eye not compensated for by the graft. Suturing in these operations also causes radial asymmetry of the cornea consequently promotes astigmatic error in this regard. Sutures also cause scarring of the corneal tissue, which scar tissue loses its transparency. Surgical correction of astigmatism is accomplished by asymmetrically altering the corneal curvatures. The effect of a peripherical distoring force may be easily visualized by imagining an inflated balloon with a spherical surface being compressed between the palms of the hands. Because the volume of air in the balloon is constant, the surface area remains constant. The previously spherical anterior surface is distorted meridianally as a result of compressing the diameter between the hands so that the curvature changes without changing the circumference of the surface. The meridian passing over the balloon between the extended fingers steepens, while the uncompressed meridian at right angles thereto flattens as its diameter lengthens in proportion to the shortening of the compressed diameter. This demonstrates the effect that may result from slight variations in the symmetrical patterns or intentional asymmetrical patterns attempted to be accomplished during surgical procedures and attendant suturing. It is thus seen that present procedures in keratorefractive techniques are best limited to situations where other more standard corrective practices are found ineffective. It is readily seen that the limiting factors in such surgical techniques is the gross complexity involved not only with multiple incisions in corneal tissue for affecting the procedures but also complex suturing patterns, resulting in gross restructuring of the eye. The eye is thus faced with a difficult job of adjusting to this trauma.

It is therefore an object of the present invention to provide a new and improved keratorefractive technique involving method and apparatus for changing the shape of the optical zone of the cornea to correct refractive error whereby a minimum disturbance is imposed on the eye system and the simplicity of the technique virtually eliminates the chance of error or further complications resulting from gross disturbances of the eye system.

SUMMARY OF THE INVENTION

With this and other objects in view of the present invention contemplates a method and apparatus involving inserting one end of a split end adjusting ring in the cornea of the eye and moving the ring in a circular path until its ends meet, whereby the ends are adjusted relative to one another until the shape of the eye has assumed a desired curvature whereupon the ends are fixedly attached to maintain the desired curvature of the cornea.

Another aspect of the invention involves an ovaloid cross sectional shape of the adjusting ring which when inserted in the cornea is arranged to have its major cross sectional axis aligned with a corneal arc extending through the anterior pole of the cornea.

An additional aspect of the invention involves a dissecting ring which has split end portions, with one end being inserted into the cornea prior to insertion of the adjusting ring. Such one end is then moved in a circular path about the interior of the cornea until it reaches the insertion point, whereupon the one end of the adjusting ring is releasably attached to the one end of the dissecting ring and the dissecting ring is then moved in a reversed circular path, pulling the now attached adjusting ring behind it until the one end of the dissecting ring has returned to the insertion point. At this time the one end of the adjusting ring has also circularly moved about the interior of the cornea until its one leading end has reached the insertion point to implant the adjusting ring in the cornea and withdraw the dissecting ring. The corneal curvature adjusting procedure and ring end fixing procedure are then performed.

Still another aspect of the invention is the shape of the one leading end of the respective dissecting ring and adjusting ring which is asymmetrically rounded into a sled shape to maintain a transverse bias on the one ends as they are moved within the corneal tissue.

Yet another aspect of the invention pertains to a connecting system for releasably attaching the leading ends of the respective dissecting and adjusting rings, including holes near the tip ends of the one end of the rings with longitudinal grooves extending from the holes to the tip ends, and an inverted "U-shaped" clip which is inserted in the holes of both rings to hold the ring ends together while they are being moved about the interior of the cornea.

Another aspect of the invention involves the use of a ring holder and moving device which is comprised of an elongated cylindrical member having a concave surface formed concentrically within its lower end and sized to fit over the curvature of the cornea, with a circular groove in the face of the concave surface, which groove is sized to hold the dissecting ring in its circular configuration, and a means for exerting a magnetic force on the dissecting ring to cause the ring to follow the rotational path of the holder when it is rotated over the eye after the one end of the dissecting ring is inserted into the corneal tissue. This magnetic force also pulls the dissecting ring toward the anterior of the corneal stroma into which it is being inserted. In addition, a pin extends outwardly from the groove and serves to engage a blunt trailing end of the dissecting ring as it is being inserted to further facilitate its movement in and about the cornea as the holder is rotated. Also, a cylindrical sleeve may be fitted over a portion of the elongated cylindrical member to facilitate holding the holding device steady as the cylindrical member is rotated in the adjusting ring insertion procedure.

Yet still another aspect of the invention resides in providing visual indication of the present shape of the cornea together with an indication of a desired shape and comparing the indications while the adjusting ring ends are being adjusted to aid in fixing the ends of the adjusting ring at a place to provide the desired corneal topography.

BRIEF DESCRIPTION OF THE DRAWINGS

FIG. 5 is a plan view of a dissecting ring showing its end portions;

FIG. 6 is a plan view of an adjustment ring showing its end portions;

FIG. 7 is an elevational view showing the inserting ends of the respective dissecting ring and adjustment rings positioned for receiving a releasable connecting clip;

FIG. 8 is an elevational view of the adjusting ring taken along lines 8—8 of FIG. 6;

FIG. 9 is a partial perspective view of the cornea of an eye with incisions for receiving the dissecting and adjusting rings and the rings positioned for releasable attachment to one another just prior to implanting the adjusting ring;

FIG. 10 is a side elevational cross sectional view of a dissecting ring holding and rotating tool; and FIG. 11 is a schematic representation of a corneascope type image superimposed with a target image for comparing the present shape of the cornea with a desired shape to permit accurate fixing of the adjustment ring to fix the shape of the cornea.

DESCRIPTION OF THE PREFERRED EMBODIMENT

Figure 1:
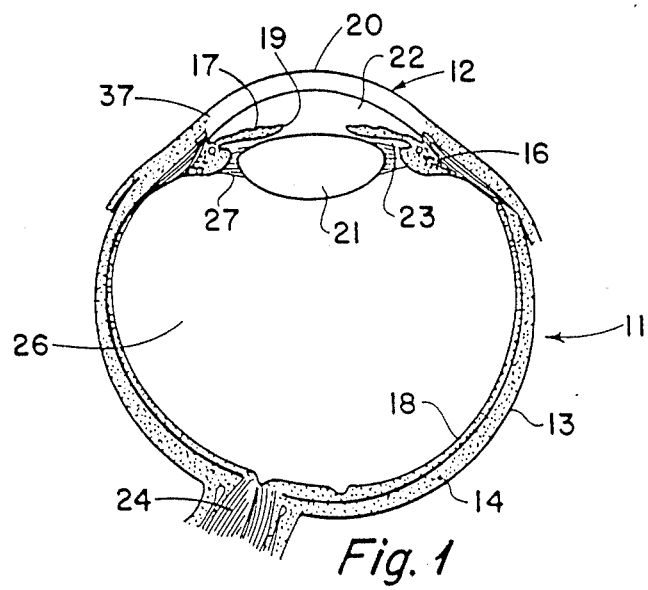
FIG. 1 is a schematic illustration of a horizontal section of the eye.

Referring first to FIG. 1 of the drawings, a horizontal section of the eye shows the globe of the eye resembling a sphere with an anterior bulged spherical portion 12 representing the cornea. Thus the eye is actually comprised of two somewhat modified spheres placed one in front of the other. The anterior of these two segments is the smaller more curved cornea.

The globe of the eye consists of three concentric coverings enclosing the various transparent media through which the light must pass before reaching the sensitive retina. The outermost covering is a fibrous protective portion the posterior five-sixths of which is white and opaque and called the sclera 13, and sometimes referred to as the white of the eye where visable to the front. The anterior one-sixth of this outer layer is the transparent cornea 12.

A middle covering is mainly vascular and nutritive in function and is comprised of the choroid 14, cibiary body 15 and iris 17. The choroid generally functions to maintain the retina. The ciliary muscle is involved in suspending the lens and accomodation of the lens. The iris is the most anterior portion of the middle covering of the eye and is arranged in a frontal plane. It is a thin circular disc corresponding to the diaphram of a camera, and is perforated near its center by a circular aperature called the pupil 19. The size of the pupil varies to regulate the amount of light which reaches the retina. It contracts also to accomodation, which serves to sharpen the focus by diminishing spherical aberration. The iris divides the space between the cornea 12 and the lens 21 into an anterior chamber 22 and posterior chamber 23. The innermost portion of covering is the retina 18, consisting of nerve elements which form the true receptive portion for visual impressions.

The retina is a part of the brain arising as an outgrowth from the fore-brain, with the optic nerve 24 serving as a fibre tract connecting the retina part of the brain with the fore-brain. A layer of rods and cones, lying just beneath a pigmented epitheluim on the anterior wall of the retina, serve as visual cells or photoreceptors which transform physical energy [light] into nerve impulses.

The vitreous 26 is a transparent gelatinous mass which fills the posterior four-fifths of the globe. At its sides it supports the ciliary body 16 and the retina 18. A frontal saucer-shaped depression houses the lens 21.

The lens 21 of the eye is a transparent bi-convex body of crystalline appearance placed between the iris 17 and vitreous 26. Its axial diameter varies markedly with accomodation. A ciliary zonule 27, consisting of transparent fibres passing between the ciliary body 16 and lens 21 serves to hold the lens in position and enable the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place on the surface of the cornea.

Figure 4:
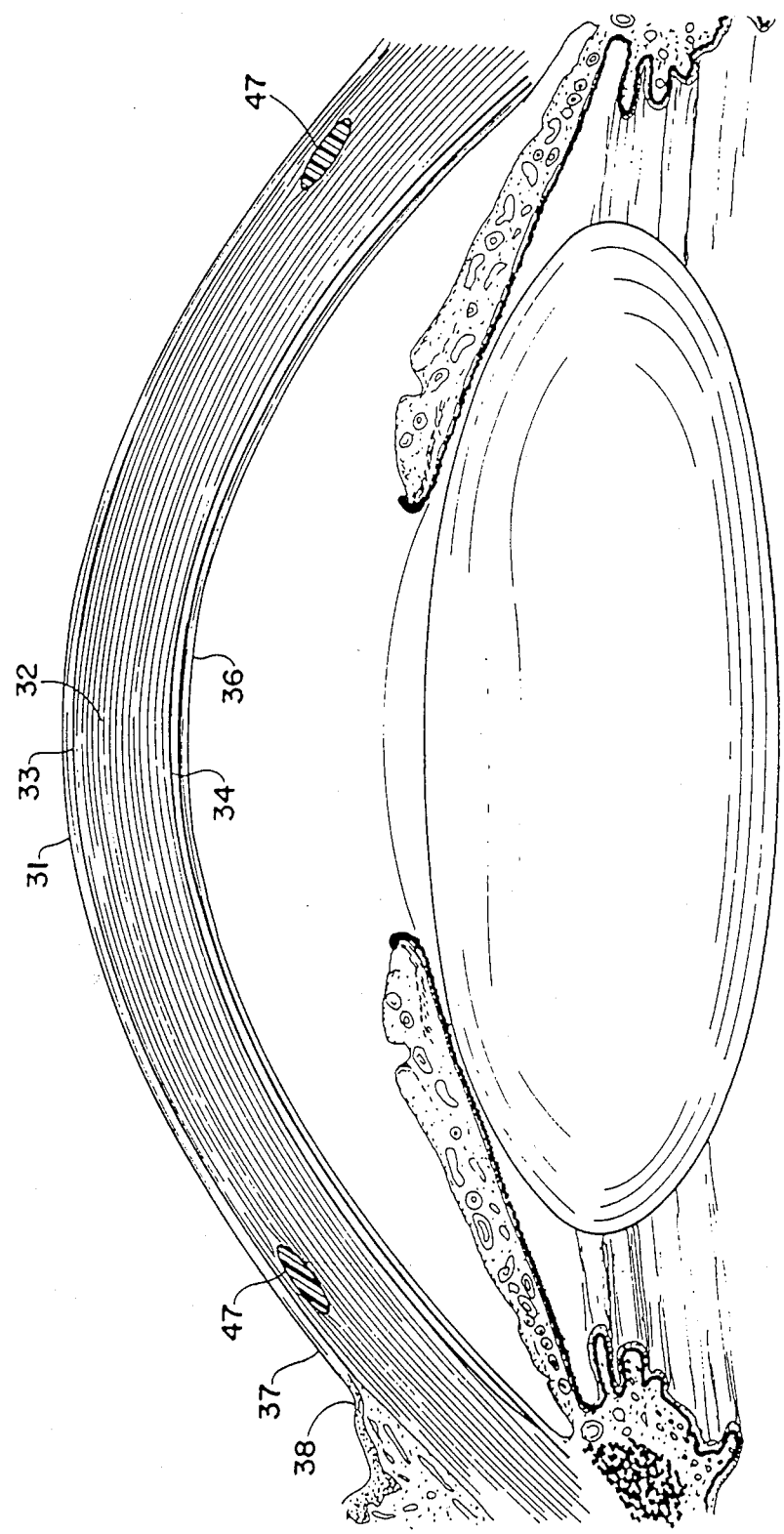
FIG. 4 is a more detailed schematic illustration of a horizontal section of the frontal portion of the eye showing an adjusting ring positioned in the stroma of the cornea.

Referring to FIG. 4, a more detailed drawing of the anterior portion of the globe shows the various layers of the cornea comprising an epitheluim 31. Epithelial cells on the surface thereof function to maintain transparency of the cornea. These epithelial cells are rich in glycogen, enzymes and acetylcholine and their activity regulates the corneal corpuscles and controls the transport of water and electrolyles through the lamellae of the stroma 32 of the cornea.

An anterior limiting lamina 33, referred to as Bowman's membrane, is positioned between the epithelium 31 and the substantia propria or stroma 32 of the cornea. The stroma is comprised of lamella having bands of fibrils parallel to each other and crossing the whole of the cornea. While most of the fibrous bands are parallel to the surface, some are oblique, especially anteriorly. The fibrous bands within alternate lamella are at a near right angle to bands in the adjacent lamella. A posterior limiting lamina 34 is referred to as Descemet's membrane. It is a strong membrane sharply defined from the stroma and resistant to pathological processes of the cornea.

The endotheluim 36 is the most posterior layer of the cornea and consists of a single layer of cells. The limbus 37 is the transition zone between the conjunctiva 38 and sclera 13 on the one hand and the cornea 12 on the other.

Figure 2:
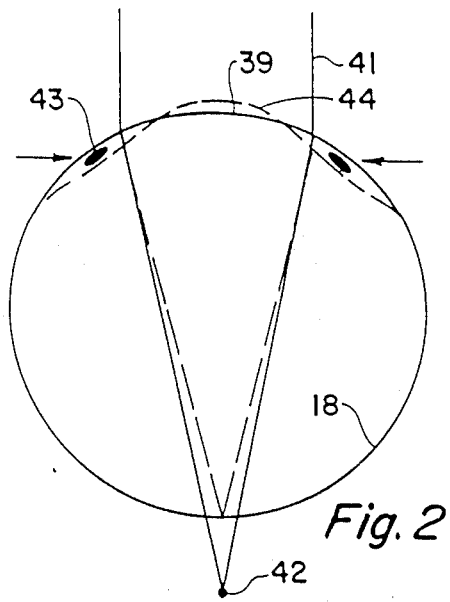
FIG. 2 is a schematic illustration of an eye system showing adjustment of the cornea to steepen the corneal slope.

Referring next to FIG. 2 of the drawings, the globe of an eye is shown having a cornea 12 with a normal curvature represented by the solid line 39. If parallel rays of light 41 pass through the corneal surface 39 of FIG. 2 they are refracted by the corneal surfaces to converge eventually near the retina 18 of the eye. The diagram of FIG. 2 discounts, for the purposes of this discussion, the refractive effect of the lens or other portions of the eye. The eye depicted in FIG. 2 is hyperopic and thus the rays of light 41 are refracted to converge at point 42 behind the retina. If a peripherial band of pressure is applied inwardly at the chord 43 of the cornea, the walls of the cornea are caused to steepen. This is because the volume of fluids within the anterior chamber 22 remains constant, thus the anterior portion of the cornea, including the optical zone (inner third of the cornea) steepens in slope to form a curvature (shown in exageration) following the dotted line 44. The rays of light 41 are then refracted from the steeper surface 44 at a greater angle to direct the refracted rays into focus at a shorter distance, such as directly on the retina 18.

Figure 3:
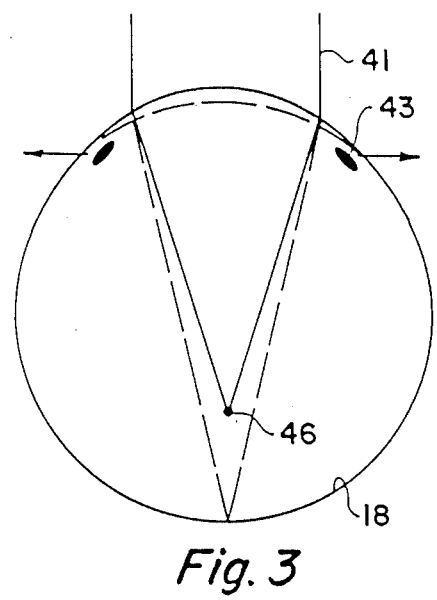
FIG. 3 is a schematic illustration of an eye system showing adjustment of the cornea to flatten the corneal slope.

FIG. 3 shows a similar eye system to that of FIG. 2 except that the so called normal corneal curvature of FIG. 3 causes the light rays 41 to refract into focus at a point 46 in the vitreous which is short of the retinal surface 18. This is typical of a myopic eye. If chord 43 of the cornea is expanded uniformly outwardly as shown by the arrows, the walls of the cornea are flattened. Light rays 41 refracted by the now flattened corneal surface will be refracted at a smaller angle and thus converge at a more distant point such as directly on the retina 18.

The methods and apparatus of the present invention are concerned with a system for adjusting an annular chord of the cornea as suggested by the processes shown in FIGURES 2 and 3 to thereby correct refractive errors of the eye. Again referring to FIG. 4, a ring 47, having an ovaloid cross sectional shape is shown implanted in the stroma layer of the cornea. By adjusting the diameter of such a ring in the cornea and fixing that diameter at a discrete value, the rays refracted by the cornea and other eye components can be brought to focus directly on the retina 18. Such a ring placed approximately at the 8 mm chord of the cornea provides a means for making such a corrective adjustment. Apparatus and methods for making this adjustment are hereinafter described.

Referring now to FIGS. 6 and 8 of the drawings, the adjusting ring 47 is comprised of a generally circular member having split end portions 48 and 49. The ring is comprised of a material which has sufficient stiffness to maintain its generally circular shape and sufficient resiliency to permit its ends 48 and 49 to be adjusted relative to one another to thereby enlarge or decrease the normal diameter of the ring at rest. The material should have properties that render it physiologically compatible with the tissue of the cornea. Two such materials are plastic type materials sold under the trade names PLEXIGLASS and SAUFLON. The cross sectional shape of the rings is that of an oval generally dimensioned to be about 1 mm across its major axis and 0.2 mm across its minor axis. The one insertion end or leading end 48 of the adjusting ring is tapered asymmetrically to a rounded tip end (See FIG. 7).

As shown in FIG. 8, the major axis of the oval ring 47 is formed at an angle sloping inwardly to the center of the ring. The angular disposition of the major axis of the ovaloid ring corresponds to the intended implantation position of the ring 47 in the cornea. The ring is implanted in the stroma 32 of the cornea as shown in FIG. 4. One function of the stroma is to transfer fluids through the eye. In order to minimize the effect of the implanted ring 47 on the transfer of fluids, the ring is positioned so that its major axis is parallel to the lamellae of the stroma. Thus the ring is implanted at a slope corresponding to the slope of a corneal arc extending through the anterior pole 20 (FIG. 1) of the cornea. This slope of the adjusting ring also corresponds to the direction of lamellae within the corneal stroma. By orienting the ring thusly, the ring may be inserted between the lamellae to produce a minimum of trauma to the eye. During the development of this procedure, a circular adjusting ring was used. It was found however that the circular ring, when expanded or contracted to adjust its size (See FIGS. 2 & 3), creates a sufficient pressure between the corneal tissue and the ring, to cause the ring to cut through the tissue. By utilizing an avaloid shape and orienting the major axis of the avaloid as shown in FIG. 4, an enlarged surface is presented in the direction of pressure of the ring to prevent cutting of the tissue. Thus the major axis of the ring acts against the lamellae of the stroma in the direction of pressure and the minor axis is aligned with the lamellae to provide a minimum of interruption to fluid flow.

FIG. 5 of the drawings shows a dissecting ring 51 which is circular in cross section and has overlapping split end portions 52 and 53. The ends of the ring overlap approximately one half a diameter of the ring. Ring 51 may be constructed of a metallic material such as stainless steel and in any event a magnetic material for purposes to be hereinafter described. Ring 51 also is provided with an asymmetrically rounded end portion 52 having a lower tapered surface to resemble the shape of a sled runner. The trailing end 53 of the dissecting ring 51 has a blunt end surface 54.

Referring now to FIG. 7 both the dissecting ring 41 and the adjusting rings have transverse substantially vertical holes 56 and 57 respectively through their ends, near the tip ends thereof. Longitudinal grooves 58 are formed in the top surface of each of the rings 47, 51 and extend from the holes 56, 57 to the respective tip ends of the rings. An inverted U-shaped clip member 61 is shown positioned in FIG. 7 for reception of its downwardly projecting leg portions 62 into the holes 56 and 57 of the dissecting and adjusting rings respectively and its body portion 63 into the longitudinal grooves 58 in the top end of the respective rings.

Referring to FIG. 10 of the drawings, a dissecting ring holding and rotating apparatus 71 is shown including a solid cylindrical rotating member 72 having a knurled upper end surface 73. The cylindrical rotating member 72 is slip fitted with a cylindrical holding sleeve 74 to permit relative rotation between the member 72 and sleeve 74. The lower end of the rotating member 72 has a concentrically arranged concave surface 76 having its concave shape as well as the proportions of the surface 76 arranged to be matingly received over the anterior corneal surface of the eye. An annular groove 77 is formed in the concave surface 76 near the peripherial edge of the rotating member 72. This groove 77 is sized to receive and hold the dissecting ring at its nominal diameter for insertion into and around the cornea at the 8 mm chord of the eye as shown in FIG. 4. This chord is located within a plane across the cornea which measures approximately 8 mm in diameter. Thus the groove 77 itself has an internal diameter of approximately 8 mm. The rotatable holding member 72 is constructed of a magnetized material or has a means for being magnetized. The magnetic nature of the member 72 holds the ring 51 in place on the tool during the keratorefractive procedure to be described. A small pin 78 is vertically arranged to project downwardly from a point in the groove. This pin contacts the trailing blunt end 54 of the dissecting ring.

The method of implanting an adjusting ring 47 within the cornea of the eye is as follows: First, a determination is made, by taking optical measurements of the eye, as to what shape the cornea should have in order for that eye to operate in an optically correct manner. FIG. 11 shows a target image comprised of indicia 81. This target grid 81 may be made by reflecting light from placido rings from a standard spherical surface the same size as the eye in question and at a fixed distance. An image is made of this "correct" topographic map of the eye, referred to herein as a target or target image. The target indicia is in the form of vertical lines or grids 81 as shown in FIG. 11 which of course may be drawn in other radial meridians as well as the horizontal meridian as shown. The spacings between the grids 81 represents a topographic survey of an eye having a corrected curvature, as pertains to the specific eye in question.

A dissecting ring 51 is next placed in the groove 77 on the concave surface 76 of the rotatable holding member 72. The blunt end 54 of ring 51 is contacted against the pin 78 extending outwardly from the groove. The magnetic attraction between the magnetic member 72 and steel ring 51 holds the ring in place on the end of the member 72. Next, working under a surgical microscope, a small (approximately 1 mm long and 0.2 mm deep) incision 82 (FIG. 9) is made in the cornea through the epithilium and Bowman's membrane. This incision is approximately the same size as the adjusting ring to be implanted. The leading end 52 of the dissecting ring 51 is then moved through the incision and into the stroma of the cornea. The holding member 72 is then rotated to progressively thread the ring around the cornea between the adjacent lamellae within the anterior portion of the stroma. The lamellae of fibrils near the anterior of the stroma are more lossely formed, making this a desirable location in the stroma for insertion of the dissecting ring and for implantation of the adjusting ring. The sled shaped nose portion on the end 52 of the dissecting ring causes the end 52 to be continuously biased upwardly sufficiently to maintain the ring 52 in a path in the anterior lamellae of the stroma. The magnetic force between the holder 72 and the dissecting ring also causes the dissecting ring to maintain its path within the anterior lamellae. Rotation of the holding member 72 is continued with the pin 78 and magnetic attraction between the ring 51 and holder 72 serving to drive the ring about the cornea until the end portion 52 reaches the incision 83. At this time, a second incision (FIG. 9) is made perpendicular to the first incision, with the second incision being approximately 1 mm long. In any event the second incision extends from a position just above the hole 57 in the dissecting ring to a normal intersection with the first incision 83. The leading end 48 of the adjusting ring 47 is then brought into position with its tip end adjacent the tip 52 of the dissecting ring now lying below the corneal surface. As shown in FIG. 7, the clip member or link 61 is now placed with its leg portions 62 projecting into the holes 56 and 57 in the respective adjusting and dissecting rings and the body portion 63 of clip 61 is passed through the second incision 82 into position in the grooves 58 in the top side of the respective rings.

Next the holding member 72 is rotated in an opposite direction pulling the leading end 48 of the adjusting ring through the incision 83 and around the circular path previously made by the insertion of the dissecting ring. The dissecting ring is moved in reverse rotation with the member 72 by means of the magnetic force between the holder 72 and ring 51. The plastic adjusting ring 47 is pulled by the metal dissecting ring. As the adjusting ring 47 is drawn into the cornea, the dissecting ring is being progressively withdrawn or "backed-out" until the leading end 48 of the adjusting ring is brought circularly back around to the incision 83, at which time the dissecting ring is fully withdrawn. The link 61 is then removed from the holes 56, 57 and slots 58 to release the connection between the dissecting and adjusting rings. The tip ends of the split ends 48, 49 of the adjusting ring are then grasped, such as by the ends of an adjustable caliper, and adjusted longitudinally endwise relative to one another to adjust the diameter of the ring and thereby bring the shape of the cornea into coincidence with the indicia 81 on the target image (FIG. 11). Also shown in FIG. 11 is an image of somewhat concentric circles 83 similar to that projected from a viewing surface by a corneascope. The rings are produced by reflecting light from placido rings onto the present corneal surface being worked on. The distances from placido rings to cornea to image surface is the same as for constructing the target image. The concentricity and spacings of the rings 83 represents the topography of the eye being worked on. By superimposing the rings 83 onto the target image while adjustment of the ends of the adjusting ring 47 is taking place, perfect corrections of the corneal shape may be affected by manipulating the ends of the adjusting ring until the indicia 81 and circles 83 are brought into coincidence. The ends 48, 49 of the adjusting ring 47 are then fixed together such as by gluing or the like to permanently fix the correct shape of the cornea.

While particular embodiments of the present invention have been shown and described, it is apparaent that changes and modifications may be made without departing from this invention in its broader aspects, and therefore, the aim in the appended claims is to cover all such changes and modifications as fall within the true spirit and scope of the invention.

What is claimed is:

1. Apparatus for rotatably inserting a dissecting ring that has a forward cutting end and a trailing end into the corneal tissue of the eye including;
   an elongated member;
   a concave concentrical surface on one end of said elongated member concentric groove means within said surface to releasably retain said dissecting ring;
   means within said concave concentrical surface to abut against said trailing end;
   surface means on at least a portion of said elongated member to facilitate rotation of said elongated member.

2. The apparatus of claim 1 wherein said elongated member is cylindrical and further including circular sleeve means arranged for receiving said elongated member therein.

3. Apparatus for inserting an adjusting ring into the corneal tissue of the eye including;
   an elongated member;
   a concave concentrical surface on one end of said elongated member;
   concentric groove means in said concave surface, said groove means is arranged to receive a split dissecting ring and further including pin means extending outwardly from said groove for engaging one end of said dissecting ring;
   surface means on at least a portion of said elongated members to facilitate rotation of said elongated member; and
   magnet means for generating a magnetic field near said one end of said elongated member.

4. Apparatus according to claim 1 including a magnet means for generating a magnetic field adjacent said concave concentrical surface.

* * * * *